United States Patent [19]

Chapura et al.

[11] Patent Number: 5,192,752
[45] Date of Patent: * Mar. 9, 1993

[54] SWALLOWABLE PHARMACEUTICAL COMPOSITIONS CONTAINING COLLOIDAL BISMUTH SUBCITRATE

[75] Inventors: Francis B. Chapura, Hamilton; Sekhar Mitra, Cincinnati, both of Ohio

[73] Assignee: The Procter & Gamble Company, Cincinnati, Ohio

[ * ] Notice: The portion of the term of this patent subsequent to Jul. 7, 2009 has been disclaimed.

[21] Appl. No.: 640,920

[22] Filed: Jan. 14, 1991

[51] Int. Cl.$^5$ .............. A61K 31/65; A61K 31/43; A61K 31/545; A61K 31/415; A61K 31/29

[52] U.S. Cl. .................. 514/152; 514/192; 514/200; 514/398; 514/503

[58] Field of Search .......... 514/503, 925, 152, 192, 514/200, 398; 424/653

[56] References Cited

U.S. PATENT DOCUMENTS

| | | | |
|---|---|---|---|
| 4,801,454 | 1/1989 | Conveney | 424/131 |
| 4,801,608 | 1/1989 | Bos et al. | 514/925 |
| 4,940,695 | 7/1990 | Conveney et al. | 514/925 |
| 5,008,256 | 4/1991 | Clitherow | 514/184 |
| 5,013,560 | 5/1991 | Stentz et al. | 424/653 |

FOREIGN PATENT DOCUMENTS

| | | |
|---|---|---|
| 206625 | 12/1986 | European Pat. Off. . |
| 206626 | 12/1986 | European Pat. Off. . |
| 206627 | 12/1986 | European Pat. Off. . |
| 282131 | 9/1988 | European Pat. Off. . |
| 282132 | 9/1988 | European Pat. Off. . |
| 437294 | 7/1991 | European Pat. Off. . |
| 1478742 | 7/1977 | United Kingdom . |
| 2220937 | 1/1990 | United Kingdom . |
| 86/05981 | 10/1986 | World Int. Prop. O. . |

OTHER PUBLICATIONS

Nwokolo et al. Aliment. Pharmacol. Therap., (1989), 3, pp. 21-28.

*Primary Examiner*—Frederick E. Waddell
*Assistant Examiner*—Raymond J. Henley, III
*Attorney, Agent, or Firm*—Kim William Zerby; Douglas C. Mohl; Richard C. Witte

[57] ABSTRACT

Oral pharmaceutical compositions in unit dosage form suitable for swallowing (especially capsules) comprising a safe and effective amount of solid Colloidal Bismuth Subcitrate (CBS), and optionally one or more pharmaceutically-acceptable carrier materials, wherein the packing density of the dosage unit is less than about 1 g/ml.

22 Claims, No Drawings

SWALLOWABLE PHARMACEUTICAL COMPOSITIONS CONTAINING COLLOIDAL BISMUTH SUBCITRATE

BACKGROUND OF THE INVENTION

The present invention relates to low density oral pharmaceutical compositions in unit dosage form suitable for swallowing comprising solid Colloidal Bismuth Subcitrate.

Solid Colloidal Bismuth Subcitrate ("CBS"; Trademark De-Nol ® of Gist-brocades N.V.) is the product of European Patent 0,075,992, corresponding to U.S. Pat. No. 4,801,608. It is also the active ingredient of British Patent 1,478,742. According to these specifications, CBS can be formulated into pharmaceutical compositions in solid dosage form for oral administration, such as tablets and capsules. Up to now only the tablet form (both chewable and swallowable tablets) has been realized and it is marketed in many countries.

The currently used swallowable tablet form of CBS has already been given to hundreds of thousands of patients and its clinical efficacy and safety are firmly established. However, recently there have been reports of a transient sharp peak of bismuth blood level in humans after the ingestion of this CBS-containing swallowable tablet, $t_{max}$ around 30 minutes (see C. U. Nwokolo et al, Aliment. Pharmacol. Therap., 3, 1989, 29-39). Since the therapeutic action of CBS is believed to be localized in the gastrointestinal tract, even a transient peak of bismuth blood level does not appear to serve any useful purpose and it is therefore desirable to minimize bismuth blood levels if possible.

It has been discovered that this currently used tablet form (having a density greater than 1 g/ml), in vitro in liquid acidic medium, has a tendency to sink to the bottom of the liquid and dissolve by first forming liquid CBS solution rather than the desired insoluble bismuth precipitate. By contrast, unit dosage forms (as according to the present invention) which are less dense than the current tablet form and also less dense than the acidic medium (approximately 1 g/ml) do not form this initial CBS liquid but rather quickly forms the desired insoluble bismuth precipitate. Interestingly, when these low density unit dosage forms are weighted to the bottom of the test liquid, again the CBS initially liquifies.

A low packing density of oral dosage units as specified above is contrary to the current tendency in the art of pharmaceutical production, which is to concentrate the oral dosage units, e.g. by compressing the contents of oral capsules to a high density (see Hard Capsules, Development and Technology, Ed. K. Ridgway 1987, chapter 9, G. C. Cole, pp. 92-103).

That the low density unit dosage form of the present invention in fact substantially reduces bismuth blood levels as predicted by these different in vitro characteristics has been confirmed by in vivo testing. The oral dosage units of the present invention, when compared to swallowable tablets comprising the same formula and dosage of CBS but with a higher density, were found to give not only a lower maximal blood plasma bismuth level ($C_{max}$), but also a lower blood plasma bismuth rise (AUC) and a lower bismuth excretion in the urine. Therefore, systemic bismuth absorption after ingestion of the dosage units of the present invention has proved to be lower than after ingestion of the prior swallowable tablets. This is contrary to what one might expect—that less dense and thereby more dispersible material would lead to more rapid dissolution and consequently to greater absorption than compressing to higher density the same material.

Thus, the oral dosage units of the present invention surprisingly give peak bismuth plasma levels and a total bismuth absorption which are lower than that of the denser dosage units.

An object of the present invention therefore is to provide an oral dosage unit suitable for swallowing comprising CBS in a therapeutically effective amount which substantially reduces bismuth absorption and thereby the above described peak in the bismuth blood levels.

This and other objects of the present invention will become readily apparent from the detailed description which follows.

All percentages and ratios used herein are by weight, and all measurements made at 25° C., unless otherwise specified.

SUMMARY OF THE INVENTION

The present invention relates to oral pharmaceutical compositions in unit dosage form suitable for swallowing comprising a safe and effective amount of solid colloidal bismuth subcitrate and, optionally, pharmaceutically-acceptable carrier materials, wherein the packing density of the pharmaceutical composition is less than about 1 g/ml.

The present invention also relates to a method for manufacturing unit dosage forms suitable for swallowing comprising solid colloidal bismuth subcitrate. Said method comprises the step of forming a unit dosage of a dry composition comprising solid colloidal bismuth subcitrate having a packing density of less than about 1 g/ml. Preferred is the method wherein a dry particulate composition comprising solid colloidal bismuth subcitrate is filled into a capsule to a packing density of less than about 1 g/ml.

The present invention further relates to methods for treating or preventing gastrointestinal disorders in humans or lower animals. These methods comprise orally administering by swallowing to a human or lower animal in need of such treatment or prevention a safe and effective amount of an oral pharmaceutical composition according to the present invention.

DETAILED DESCRIPTION OF THE INVENTION

(1) Oral Pharmaceutical Compositions

The oral pharmaceutical compositions of the present invention comprise colloidal bismuth subcitrate ("CBS") in unit dosage forms suitable for swallowing (e.g., tablets and, especially, capsules) wherein the packing density of the composition is less than about 1 g/ml. Preferably, these compositions comprise the CBS and a pharmaceutically-acceptable carrier material(s).

The term "packing density," as used herein, means the weight of the drug mixture (active CBS ingredient plus carrier materials) in grams divided by the volume occupied by the dose form expressed in milliliters, and, in case of a filled capsule form, excludes the volume and weight of the capsule container. Thus, the packing density can be varied by varying the types and amounts of excipients added to the CBS and especially by varying the pressure used in compressing the units. Oral pharmaceutical compositions herein have packing density of less than about 1 g/ml, preferably within the range of from about 0.05 g/ml to less than about 1 g/ml, more preferably from about 0.25 g/ml to about 0.9 g/ml, and most preferably from about 0.5 g/ml to about 0.75 g/ml.

The particular agents for use herein, as well as the levels and amounts preferred therefor, are described in greater detail hereinafter.

(a) Colloidal Bismuth Subcitrate

Colloidal bismuth Subcitrate ("CBS") is described in *The Merck Index*, 11*th Edition* (1989), item 1296 (incorporated herein by reference in its entirety), to have the approximate molecular formula of $K_3(NH_4)_2[Bi_6O_3(OH)_5(C_6H_5O_7)_4]$. The preparation and use of CBS is described in detail in U.S. Pat. No. 4,801,608, to Bos et al, issued Jan. 31, 1989; and Great Britain patent specification 1,478,742, published Jul. 6, 1977 by Gistbrocades, N.V., the disclosures of both these patents being incorporated herein by reference in their entirety. The CBS used in the compositions of the present invention (preferably including any optional carrier materials) is preferably in the form of granules or powders, having a preferred particle size of less than about 1.5 mm.

The oral pharmaceutical compositions herein comprise a safe and effective amount of CBS, typically in the amount of from about 30 mg to about 600 mg per dosage unit, and preferably from about 37.5 mg to about 300 mg per dosage unit. As a percentage of the oral pharmaceutical compositions, CBS typically comprises from about 1% to about 100%, and preferably from about 25% to about 99%, by weight of the composition.

(b) Pharmaceutically-Acceptable Carrier Materials

The oral pharmaceutical compositions herein may also optionally comprise one or more pharmaceutically-acceptable carrier materials. The term "pharmaceutically-acceptable carrier materials," as used herein, means one or more compatible solid or liquid filler diluents or encapsulating substances which are suitable for oral administration to a human or lower animal. The term "compatible," as used herein, means that the components of the oral pharmaceutical composition are capable of being commingled with the CBS, and with each other, in a manner such that there is no interaction which would substantially reduce the pharmaceutical efficacy of the pharmaceutical composition under ordinary use situations by swallowing the composition. Pharmaceutically-acceptable carrier materials must, of course, be of sufficiently high purity and sufficiently low toxicity to render them suitable for oral administration to the human or lower animal being treated.

To the CBS may be added any of the pharmaceutically-acceptable carrier materials known in the art, which are compatible with CBS, such as:

diluents, like lactose, starch, microcrystalline cellulose, sorbitol, mannitol, dibasic calcium phosphate dihydrate, calcium sulfate dihydrate, sucrose-based diluents and mixtures thereof;

binders, like acacia, cellulose derivatives, gelatin, glucose, polyvinylpyrrollidone, starch, sucrose, sorbitol, tragacanth, sodium alginate and mixtures thereof;

disintegrants, like microcrystalline cellulose and cellulose derivatives, starch and its derivatives, alginic acid and its derivatives, ion-exchange resins, cross-linked sodium carboxymethyl cellulose, sodium starch glycolate, cross-linked polyvinylpyrrollidone and formaldehyde-caseine;

lubricants, antiadherents and glidants, like magnesium-, calcium- and sodium stearates, stearic acid, hydrogenated castor oil, talc, water, polyethylene glycol, sodium laryl sulfate, magnesium laryl sulfate and silica.

Furthermore, the pharmaceutically-acceptable carrier materials may also comprise one or more auxiliary medicaments, preferably those which are intended to act in combination with it, such as non-steroidal anti-inflammatory compounds, $H_2$-antagonists, cytoprotectants (e.g., sucralfate), and synthetic prostaglandins. In particular the dosage units may contain antimicrobially effective medicaments such as antibiotics and chemotherapeutic compounds, more in particular medicaments effective against *Campylobacter pylori* (recently renamed *Helicobacter pylori*), such as the antimicrobially effective imidazoles, in particular metronidazole and tinidazole, penicillins, cephalosporins, tetracyclines, chinolones and macrolides. The dosage of the optionally present auxiliary medicaments will depend on the effectivity of the particular medicament used. Optional auxiliary medicaments useful herein are described in detail in: European Patent Application Publication No. 206,625, published Dec. 30, 1986, by Marshall; and International Publication No. WO 86/05981, published Oct. 23, 1986, by Borody, the disclosures of both these publications being incorporated herein by reference in their entirety.

The most preferred oral dosage units according to the invention are capsules, although tablets having a low density as defined above are also possible. The material of swallowable capsules according to the invention may be any of those known in the art, such as gelatine, modified starches, such as hydroxyalkyl starch, and cellulose derivatives, such as cellulose ethers, e.g. methyl cellulose. Preferably, the capsule material and size of the capsule are chosen such that the capsule unit dosage form filled with the drug mixture has a density of less than about 1 g/ml. Gelatine capsules can be soft and hard. The dosage units according to the invention may be further coated in order to provide for controlled release.

The oral pharmaceutical compositions herein preferably comprise from about 3 mg to about 1000 mg, more preferably from about 20 mg to about 150 mg, of pharmaceutically-acceptable carrier material per 100 mg of CBS. As a percentage of the oral pharmaceutical compositions, pharmaceutically-acceptable carrier materials comprise from about 0% to about 99%, and preferably from about 1% to about 75%, by weight of the composition.

The method of manufacturing unit dosage forms suitable for swallowing comprising CBS, according to the present invention, preferably comprises the step of forming a unit dosage of a dry composition comprising CBS having a packing density of less than about 1 g/ml. Preferred is the method wherein a dry particulate composition (e.g., granulate; powder) comprising CBS is filled into a capsule to a packing density of less than about 1 g/ml.

(2) Methods for Treating or Preventing Gastrointestinal Disorders

Another aspect of the present invention is methods for treating or preventing gastrointestinal disorders in humans or lower animals. Such methods comprise orally administering by swallowing, to a human or lower animal in need of such treatment or prevention, a safe and effective amount of an oral pharmaceutical composition according to the present invention.

The term "gastrointestinal disorder," as used herein, encompasses any disease or other disorder of the gastrointestinal tract, preferably the upper gastrointestinal tract, of a human or lower animal treatable or preventable by the CBS useful herein. The term "upper gastrointestinal tract," as used herein, is defined to include the esophagus, the stomach, the duodenum, and the jejunum. Such upper gastrointestinal tract disorders include, for example: disorders not manifested by presence of ulcerations in the gastric mucosa (herein "non-ulcerative gastrointestinal disorders"), including chronic or atrophic gastritis, non-ulcer dyspepsia, esophageal reflux disease and gastric motility disorders; and "peptic ulcer disease," i.e., gastric, duodenal and jejunal ulcers. Included herein are diseases or disorders caused or mediated by *Helicobacter pylori*.

The phrase "safe and effective amount," as used herein, means an amount of CBS high enough to significantly positively modify the condition to be treated but low enough to avoid serious side effects (at a reasonable benefit/risk ratio), within the scope of sound medical judgment. The safe and effective amount of the oral pharmaceutical composition of the present invention will vary with the particular condition being treated, the age and physical condition of the patient being treated, the severity of the condition, the duration of treatment, the nature of concurrent therapy, the particular pharmaceutically-acceptable carrier materials utilized, and like factors within the knowledge and expertise of the attending physician. The methods of the present invention typically involve administering from about 100 mg to about 4800 mg of CBS per day, and preferably from about 200 mg to about 1200 mg per day.

The following examples further describe and demonstrate the present invention. The examples are given solely for the purpose of illustration, and are not to be construed as limitations of the present invention since many variations thereof are possible without departing from its spirit and scope.

EXAMPLE 1

CBS is prepared according to European Patent 0,075,992 and U.S. Pat. No. 4,801,608 (both incorporated herein by reference in their entirety), and is used to prepare tablets and capsules as follows.

Uncoated swallowable tablets containing CBS are produced as follows: 100 kg of CBS is granulated with 23.8 kg of corn starch using 5.85 kg of povidone K30 dissolved in 51.0 kg of ethanol. The granulate, having a particle size of less than 1 mm, is blended with 7.8 kg of polacrilin potassium, 1.98 kg of polyethylene glycol 6000 and 0.66 kg of magnesium stearate, and is compressed into tablets.

Coated swallowable tablets containing CBS are produced by filmcoating the above described compressed tablets with about 12 mg hydroxypropyl methylcellulose and about 2 mg polyethylene glycol per tablet. These tablets are representative of commercially used De-Nol ® swallowable tablets.

Reduced density swallowable capsules according to the present invention (having packing densities of 0.6 g of CBS composition/ml and 0.86 g of CBS composition/ml) are produced using the granulate for uncoated swallowable tablets as described above, filled into hard gelatin capsules No. 0, using a rotary capsule filling machine. The packing density of the capsule content is adjusted by settings of the piston within the dosator.

The densities of the uncoated and coated tablets and of the contents of the two different capsules are calculated with respect to the amount of CBS-containing composition per units of volume. The results are presented in the following Table 1:

TABLE 1

|  | Packing volume | Packing density (CBS-containing composition/volume) |
|---|---|---|
| Tablet, uncoated | 0.25 ml | 1.7 g/ml |
| Tablet, coated | 0.25 ml | 1.7 g/ml |
| Reduced Density Capsule #1 | 0.70 ml | 0.6 g/ml |
| Reduced Density Capsule #2 | 0.50 ml | 0.86 g/ml |

EXAMPLE 2

Bismuth absorption in dogs

Healthy fasted dogs (Beagles) are given a single dose of coated tablets or the reduced-density capsules #1 of Example 1. The dogs are each dosed with 2 tablets or 2 capsules, giving a total dose of 600 mg CBS per dog. After ingestion, blood samples are taken at 9 intervals up to 8 hours. The bismuth content is measured in the blood by atomic absorption.

In dogs the reduced density capsules according to the present invention give a lower systemic bismuth absorption (for both the "blood Cmax", which is the maximum bismuth blood level measured at a time after ingestion, and the "blood AUC", which is the Area Under bismuth concentration-time Curve, over an 8 hour period after dosing) than does the prior art tablet dosage form having the same composition but compressed to a higher density.

EXAMPLE 3

Bismuth absorption in humans

Healthy fasted human volunteers are dosed with the uncoated and coated tablets and the two different capsules of Example 1. The volunteers are each dosed with 2 tablets or 2 capsules, giving a total dose of 600 mg CBS per volunteer. After ingestion blood samples are taken at several intervals up to 3 hours, and the urine is collected for 3 hours. The bismuth content is measured in the blood plasma and in the urine by atomic absorption.

In humans the reduced density capsules of the present invention give a much lower systemic bismuth absorption (for both blood Cmax and blood AUC, as well as for bismuth in urine) than does the prior art dosage form. Furthermore, there appears to be a reverse relationship between the density of the dosage form and the amount of systemic bismuth absorption therefrom, with compositions of packing density less than about 1 g/ml having substantially less bismuth absorbed than the prior art tablet having packing density above 1 g/ml.

Oral administration of the reduced density capsules of the present invention is very effective for treating patients suffering from ulcers and/or *Helicobacter pylori* infection.

What is claimed is:

1. An oral pharmaceutical composition in solid unit dosage form suitable for swallowing comprising a safe and effective amount of solid colloidal bismuth subcitrate and, optionally, pharmaceutically-acceptable carrier materials, wherein the packing density of the pharmaceutical composition is less than about 1 g/ml.

2. The oral pharmaceutical composition according to claim 1 wherein the packing density is within the range of from about 0.05 g/ml to less than about 1 g/ml.

3. The oral pharmaceutical composition according to claim 2 wherein each dosage unit comprises from about 30 to about 600 mg of solid colloidal bismuth subcitrate.

4. The oral pharmaceutical composition according to claim 1 further comprising at least one auxiliary medicament.

5. The oral pharmaceutical composition according to claim 4 wherein the auxiliary medicament comprises at least one antimicrobial medicament safe and effective against Helicobacter pylori.

6. An oral pharmaceutical composition in solid unit dosage form suitable for swallowing comprising:
  (a) from about 1% to about 100% solid colloidal bismuth subcitrate; and
  (b) from about 0% to about 99% pharmaceutically-acceptable carrier materials;
and wherein the packing density of the pharmaceutical composition is less than about 1 g/ml.

7. The oral pharmaceutical composition in solid unit dosage form according to claim 6 comprising:
  (a) from about 25% to about 99% solid colloidal bismuth subcitrate;
  (b) from about 1% to about 75% pharmaceutically-acceptable carrier materials;
and wherein the packing density of the pharmaceutical composition is within the range of from about 0.25 g/ml to less than about 0.9 g/ml.

8. The oral pharmaceutical composition according to claim 7 in solid unit dosage form of a capsule.

9. The oral pharmaceutical composition according to claim 6 further comprising at least one antimicrobial medicament safe and effective against Helicobacter pylori.

10. The oral pharmaceutical composition according to claim 9 comprising at least one antimicrobial medicament safe and effective against Helicobacter pylori selected from the group consisting of metronidazole, tinidazole, penicillin, cephalosporin, tetracycline, chinolones, macrolides, and mixtures thereof.

11. An oral pharmaceutical composition in solid unit dosage form of a capsule suitable for swallowing comprising:
  (a) from about 25% to about 99% solid colloidal bismuth subcitrate; and
  (b) from about 1% to about 75% pharmaceutically-acceptable carrier materials;
and wherein the pharmaceutical composition is filled into a capsule to a packing density within the range of from about 0.5 g/ml to about 0.75 g/ml.

12. The oral pharmaceutical composition according to claim 11 wherein the capsule container itself is made of material selected from the group consisting of gelatin, modified starch and cellulose derivative, and wherein further the capsule dosage unit has a packing density of less than about one g/ml.

13. The oral pharmaceutical composition according to claim 11 further comprising at least one antimicrobial medicament safe and effective against Helicobacter pylori selected from the group consisting of metronidazole, tinidazole, penicillin, cephalosporin, tetracycline, chinolones, macrolides, and mixtures thereof.

14. A method for treating or preventing gastrointestinal disorders in humans or lower animals, said method comprising orally administering by swallowing to a human or lower animal in need of such treatment or prevention a safe and effective amount of an oral pharmaceutical composition according to claim 1.

15. A method for treating or preventing gastrointestinal disorders in humans or lower animals, said method comprising orally administering by swallowing to a human or lower animal in need of such treatment or prevention a safe and effective amount of an oral pharmaceutical composition according to claim 4.

16. A method for treating or preventing gastrointestinal disorders in humans or lower animals, said method comprising orally administering by swallowing to a human or lower animal in need of such treatment or prevention a safe and effective amount of an oral pharmaceutical composition according to claim 5.

17. A method for treating or preventing gastrointestinal disorders in humans or lower animals, said method comprising orally administering by swallowing to a human or lower animal in need of such treatment or prevention a safe and effective amount of an oral pharmaceutical composition according to claim 9.

18. A method for treating or preventing gastrointestinal disorders in humans or lower animals, said method comprising orally administering by swallowing to a human or lower animal in need of such treatment or prevention a safe and effective amount of an oral pharmaceutical composition according to claim 10.

19. A method for treating or preventing gastrointestinal disorders in humans or lower animals, said method comprising orally administering by swallowing to a human or lower animal in need of such treatment or prevention a safe and effective amount of an oral pharmaceutical composition according to claim 11.

20. A method for treating or preventing gastrointestinal disorders in humans or lower animals, said method comprising orally administering by swallowing to a human or lower animal in need of such treatment or prevention a safe and effective amount of an oral pharmaceutical composition according to claim 13.

21. A method for manufacturing unit dosage forms suitable for swallowing, said method comprising the step of forming a unit dosage of a dry composition comprising solid colloidal bismuth subcitrate having a packing density of less than about 1 g/ml.

22. The method according to claim 21 wherein a dry particulate composition comprising solid colloidal bismuth subcitrate is filled into a capsule to a packing density of less than about 1 g/ml.

* * * * *